United States Patent
Günzburg et al.

(12) 
(10) Patent No.: US 6,730,511 B1
(45) Date of Patent: May 4, 2004

(54) VECTORS THAT REPRESS HETEROLOGOUS PROMOTER ACTIVITY

(75) Inventors: Walter H. Günzburg, Mödling (AT); Brian Salmons, Mödling (AT)

(73) Assignee: GSF-Forschungszentrum Fuer Umwelt und Gesendheit GmbH, Neuherberg (DE)

( * ) Notice: Subject to any disclaimer, the term of this patent is extended or adjusted under 35 U.S.C. 154(b) by 0 days.

(21) Appl. No.: 08/925,214

(22) Filed: Sep. 8, 1997

Related U.S. Application Data

(63) Continuation of application No. PCT/EP96/01002, filed on Mar. 8, 1996.

(30) Foreign Application Priority Data

Mar. 9, 1995 (DK) ................................................ 0244/95

(51) Int. Cl.[7] .............................................. C12N 15/74
(52) U.S. Cl. ................... 435/320.1; 514/44; 424/199.1; 424/207.1
(58) Field of Search ............................. 435/320.1, 69.1, 435/91.1, 235.1, 91.33, 456, 455; 514/44; 424/199.1, 207.1, 9.32; 536/23.72, 24.1, 23.1

(56) References Cited

PUBLICATIONS

Kaplitt et al. 1995. Viral Vectors. Academic Press, Inc. San Diego, CA; pp. 215–216, and 229.*
Dorland's Illustrated Medical Dictionary. 28th edition. W.B. Saunders Company. 1994. p. 1373.*
Wintersperger et al. 1993 Journal of Cellular Biochemistry Supplement 17D p. 54, Mar. 1993.*
Jane et al 1998 Annals of Medicine 30(5) 413–5, Oct. 1998.*
Winslow, G.M., et al., "Processing and Major Histocompatibility Complex Binding of the MTV7 Superantigen," *Immunity,* 1:23–33 (1994).
Brandt–Carlson, C., et al., "Phylogenetic and Structural Analyses of MMTV LTR ORF Sequences of Exogenous and Endogenous Origins," *Virology,* 193:171–185 (1993).
Acha–Orbea, H., et al., "Subversion of host immune responses by viral superantigens," *Trends in Microbiol.,* 1:32–34 (1993).
Mohan, N., et al., "Production and Characterization of an Mls–1–specific Monoclonal Antibody," *J. Exp. Med,* 177:351–358 (1993).
Krummenacher, C., et al., "The Mouse Mammary Tumor Virus Long Terminal Repeat Encodes a 47 kDa Glycoprotein with a Short Half–Life in Mammalian Cells," *Molecular Immunology,* 30(13):1151–1157 (1993).
Günzburg, W.H., et al., "Endogenous superantigen expression controlled by a novel promoter in the MMTV long terminal repeat," *Nature,* 364:154–158 (1993).
Winslow, G.M., et al., "Detection and Biochemical Characterization of the Mouse Mammary Tumor Virus 7 Superantigen (Mls–1ª)," *Cell,* 71:719–730 (1992).

Knight, A.M., et al., "Biochemical analysis of the mouse mammary tumor virus long terminal repeat product. Evidence for the molecular structure of an endogenous superantigen," *Eur. J. Immunol.,* 22:879–882 (1992).
Korman, A.J., et al., "The mouse mammary tumour virus long terminal repeat encodes a type II transmembrane glycoprotein," *The EMBO Journal,* 11(5):1901–1905 (1992).
Huber, B.T., "Mls genes and self–superantigens," *TIG,* 8(11):399–402 (1992).
Pullen, A.M., et al., "The Open Reading Frames in the 3' Long Terminal Repeats of Several Mouse Mammary Tumor Virus Integrants Encode Vβ3–specific Superantigens," *J. Exp. Med.,* 175:41–47 (1992).
Günzburg, W.H., et al., "Factors controlling the expression of mouse mammary tumour virus," *Biochem. J.,* 283:625–632 (1992).
Acha–Orbea, H., et al., "Clonal deletion of Vβ14–bearing T cells in mice transgenic for mammary tumour virus," *Nature,* 350:207–211 (1991).
Choi, Yongwon, et al., "A superantigen encoded in the open reading frame of the 3' long terminal repeat of mouse mammary tumour virus," *Nature,* 350:203–207 (1991).
Brandt–Carlson, C., et al., "Detection and Characterization of a Glycoprotein Encoded by the Mouse Mammary Tumor Virus Long Terminal Repeat Gene," *Journal of Virology,* 65(11):6051–6060 (1991).
Salmons, B., et al., "Current perspectives in the biology of mouse mammary tumour virus," *Virus Research,* 8:81–102 (1987).
Salmons, B., et al., "naf, a trans–Regulating Negative–Acting Factor Encoded within the Mouse Mammary Tumor Virus Open Reading Frame Region," *Journal of Virology,* 64(12):6355–6359 (1990).
Hornsby, P.J., et al., "A Modified Procedure for Replica Plating of Mammalian Cells Allowing Selection of Clones Based on Gene Expression," *BioTechniques,* 12(2):244–249 (1992).
Wintersperger, S., et al., "Negative–acting factor and superantigen are separable activities of the mouse mammary tumor virus long terminal repeat," *Proc. Natl. Acad. Sci. USA,* 92:2745–2749 (1995).
Salmons, B., et al., "Production of Mouse Mammary Tumor Virus upon Transfection of a Recombinant Proviral DNA into Cultured Cells," *Virology,* 144:101–114 (1985).
Donehower, L.A., et al., "Regulatory and Coding Potential of the Mouse Mammary Tumor Virus Long Terminal Redundancy," *Journal of Virology,* 37(1):226–238 (1981).
Günzburg, W.H., et al., "Retroviral Vectors Directed to Predefined Cell Types for Gene Therapy," *Biologicals,* 23:5–12 (1995).

* cited by examiner

*Primary Examiner*—James Housel
*Assistant Examiner*—Shanon Foley
(74) *Attorney, Agent, or Firm*—Hamilton, Brook, Smith & Reynolds, P.C.

(57) ABSTRACT

The invention refers to a novel recombinant vectors useful for gene therapy of viral infections and of diseases associated with B and T cells. The present invention relates, furthermore, to novel usages of the two products of the open reading frame of mouse mammary tumour virus.

44 Claims, 9 Drawing Sheets supertransfected constructs

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 58 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:1:

```
GAACAGCATA TGCAAAATAG ATACAGAGTG CCTTGCGAGA GAGCCTTGAC CAAGTGCA        58
```

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:2:

```
CGCAGATCTT AGCTTAAGTA ACGCCATT                                          28
```

(2) INFORMATION FOR SEQ ID NO:3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:3:

```
CGCACTAGTT CCGCCAGATA CAGAG                                             25
```

(2) INFORMATION FOR SEQ ID NO:4:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:4:

```
GAGGTACGCA GCGGAACA                                                     18
```

(2) INFORMATION FOR SEQ ID NO:5:

(i) SEQUENCE CHARACTERISTICS:
      (A) LENGTH: 18 base pairs
      (B) TYPE: nucleic acid
      (C) STRANDEDNESS: single
      (D) TOPOLOGY: linear -continued

```
        (ii) MOLECULE TYPE: other nucleic acid
              (A) DESCRIPTION: /desc = "DNA"

(xi) SEQUENCE DESCRIPTION: SEQ ID NO:5:

TGATGGGCTC ATCCGTTT                                                         18
```

VECTORS THAT REPRESS HETEROLOGOUS PROMOTER ACTIVITY

RELATED APPLICATIONS

This application is a continuation of PCT/EP96/01002, filed Mar. 8, 1996, which claims priority to Danish patent application DK 0244/95 filed Mar. 9, 1995. The teachings of PCT/EP96/01002 and DK 0244/95 are incorporated herein by reference in their entirety.

BACKGROUND OF THE INVENTION

Mouse mammary tumour virus (MMTV) is a retrovirus that is associated with mammary tumorigenesis in susceptible mice (Salmons, B. and Gűzburg, W. H., *Virus Res.*, 8:81–102, 1987). The virus is transmitted from the mother mouse to the suckling offspring via the milk. In addition to the usual retroviral genes gag, pol and env, the Long Terminal Repeat (LTR) of Mouse Mammary Tumour Virus (MMTV) contains an open reading frame (ORF) (Donehower, L. A. et al., *J. Virol.*, 37:226–238, (1981); Kennedy, N. et al., *Nature*, 295:622–624 (1982)) which is highly conserved between different MMTV isolates (Brandt-Carlson, C. et al., *Virology*, 193:171–185 (1993)). Although ORF specific transcripts have yet to be cloned, in part due to their low abundance, a splice acceptor site has been mapped immediately upstream of the 3' LTR which is presumed to generate putative 1.7 kb ORF transcripts (Wheeler, D. A., et al., *J. Virol.*, 46:42–49 (1983); van Ooyen, A. J. et al., *J. Virol.*, 46:362–370 (1983)). Recently, a novel promoter has been identified in the MMTV 5'LTR and transcripts initiating from this promoter also splice to the ORF acceptor site (Gűzburg, W. H. et al., *Nature*, 364:154–158 (1993)), increasing the potential for diversity of ORF related products.

Two biological activities, defined by functional assays, have been ascribed to products of the ORF. One of these activities is a transcriptional repressor, Naf, which down-regulates in trans expression from MMTV based constructs (Salmons, B., et al., *J. Virol.*, 64:6355–6359, (1990); Gűzburg, W. H. and Salmons, B., *Biochem. J.*, 283:625–632 (1992)). The second activity displayed by the MMTV ORF is a superantigen. (Sag) activity (Choi, Y., et al., *Nature*, 350:203–207 (1991); Acha-Orbea, H., et al., *Nature*, 350:207–211 (1991)). Expression of Sag in vivo results in the stimulation and growth, followed by deletion, of reactive T cells (reviewed in Acha-Orbea, H. and MacDonald, H. R., *Trends in Microbiology*, 1:32–34 (1993)). This effect is specific in that the Sag of a given MMTV variant interacts with specific classes of the twenty described V13 chains of the T cell receptor (Pullen, A. M., et al., *J. Exp. Med.*, 175:41–47 (1992), Huber, B. T., *Trends in Genetics*, 8:399–402 (1992)).

The viral Sag has been shown to be a type II membrane anchored glycoprotein of 45 KDa by in vitro translation studies (Korman, A. J., et al., *The EMBO J.*, 11:1901–1905 (1992), Knight, A. M., et al., *Eur. J. Immunol.*, 175:879–882 (1992)). Further, Sag proteins of 45/47 kDa have also been synthesized in baculovirus (Brandt-Carlson, C. and Butel, J. S., *J. Virol.*, 65:6051–6060 (1991); Mohan, N. et al., *J. Exp. Med.*, 177:351–358 (1993)) and vaccinia virus (Krummenacher, C. and Diggelmann, H., *Mol. Immunol.*, 30:1151–1157 (1993)) expression systems. This 45/47 kDa glycoprotein may require processing to a 18 kDa cleavage product (Winslow, G. M. et al., *Cell*, 71:719–730 (1992)). A Sag specific monoclonal antibody detects Sag expression on LPS-activated, but not nonstimulated, B cells even though the latter cells express a functional Sag. Thus undetectable levels of Sag are sufficient for superantigen activity ((Winslow, G. M. et al., *Cell*, 71:719–730 (1992); Winslow, G. M. et al., *Immunity*, 1:23–33 (1994)).

The use of retroviral vectors (RV) for gene therapy has received much attention and currently is the method of choice for the transferral of therapeutic genes in a variety of approved protocols both in the USA and in Europe (Kotani, H., et al., *Human Gene Therapy*, 5:19–28 (1994)). However, most of these protocols require that the infection of target cells with the RV carrying the therapeutic gene occurs in vitro, and successfully infected cells are then returned to the affected individual (Rosenberg, S. A., et. al., *Human Gene Therapy*, 3:75–90 (1992), Anderson, W. F., *Science*, 256:808–813 (1992)). Such ex vivo gene therapy protocols are ideal for correction of medical conditions in which the target cell population can be easily isolated (e.g., lymphocytes). Additionally the ex vivo infection of target cells allows the administration of large quantities of concentrated virus which can be rigorously safety tested before use.

Unfortunately, only a fraction of the possible applications for gene therapy involve target cells that can be easily isolated, cultured and then reintroduced. Additionally, the complex technology and associated high costs of ex vivo gene therapy effectively preclude its disseminated use world-wide. Future facile and cost-effective gene therapy will require an in vivo approach in which the viral vector, or cells producing the viral vector, are directly administered to the patient in the form of an injection or simple implantation of RV producing cells.

This kind of-in vivo approach-, of course, introduces a variety of new problems. First of-all, and above all, safety consideration have to be addressed. Virus will be produced, possibly from an-implantation of virus producing cells, and there will be-no opportunity to precheck the produced virus. It is important to be aware of the finite risk involved in the use of such systems, as well as trying to produce new systems that minimize this risk. The essentially random integration of the proviral form of the retroviral genome into the genome of the infected cell led to the identification of a number of cellular proto-oncogenes by virtue of their insertional activation (Varmus, H. "Retroviruses", *Science*, 240:1427–1435 (1988)). The possibility that a similar mechanism may cause cancers in patients treated with RVs carrying therapeutic genes intended to treat other preexistent medical conditions, has posed a recurring ethical problem. Most researchers would agree that the probability of the replication defective RV, such as all those currently used, integrating. into or near a cellular gene involved in controlling cell proliferation is vanishingly small. However, it is generally also assumed that the explosive expansion of a population of replication competent retrovirus from a single infection event, will eventually provide enough integration events to make such a phenotypic integration a very real possibility.

Retroviral vector systems are optimized to minimize the chance of replication competent virus being present. However, it has been well documented that recombination events between components of the RV system can lead to the generation of potentially pathogenic replication competent virus and a number of generations of vector systems have been constructed to minimize the risk of recombination (Salmons, B. and Günzburg, W. H., *Human Gene Therapy*, 4:129–141 (1993)). However, little is known about the finite probability of these events. Since it will never be possible to reduce the risk associated with this or other viral vector systems to zero, an informed risk-benefit decision will always have to be taken. Thus it becomes very important to empirically: determine the chance of (Donehower, L. A. et al., *J. Virol.*, 37:226–238, (1981)) insertional disruption or activation of single genes by retrovirus integration and (Kennedy, N. et al., *Nature*, 295:622–624 (1982)) the risk of generation of replication competent virus by recombination in current generations of packaging cell lines. A detailed examination of the mechanism by which these events occur will also allow the construction of new types of systems designed to limit these events.

A further consideration for practical in vivo gene therapy, both from safety considerations as well as from an efficiency and from a purely practical point of view, is the targeting of RVs. It is clear that therapeutic genes carried by vectors should not be indiscriminately expressed in all tissues and cells, but rather only in the requisite target cell. This is especially important if the genes to be transferred are toxin genes aimed at ablating specific tumour cells. Ablation of other, nontarget cells would obviously be very undesirable. Targeting of the expression of carried therapeutic genes can be achieved by a variety of means.

Retroviral vector systems consist of two components:

1. the retroviral vector itself is a modified retrovirus (vector plasmid) in which the genes encoding for the viral proteins have been replaced by therapeutic genes optionally including marker genes to be transferred to the target cell. Since the replacement of the genes encoding for the viral proteins effectively cripples the virus it must be rescued by the second component in the system which provides the missing viral proteins to the modified retrovirus.

The second component is:

2. a cell line that produces large quantities of the viral proteins, however lacks the ability to produce replication competent virus. This cell line is known as the packaging cell line and consists of a cell line transfected with a second,plasmid carrying the genes enabling the modified retroviral vector to be packaged. This plasmid directs the synthesis of the necessary viral proteins required for virion production.

To generate the packaged vector, the vector plasmid is transfected into the packaging cell line. Under these conditions the modified retroviral genome including the inserted therapeutic and optional marker genes is transcribed from the vector plasmid and packaged into the modified retroviral particles (recombinant viral particles). A cell infected with such a recombinant viral particle cannot produce new vector virus since no viral proteins are present in these cells. However, the vector carrying the therapeutic and marker genes is present and these can now be expressed in the infected cell.

Promoter Conversion Vectors

The retroviral genome consists of an RNA molecule with the structure R-U5-gag-pol-env-U3-R (FIG. 6). During the process of reverse transcription, the U5 region is duplicated and placed at the right hand end of the generated. DNA molecule, whilst the U3 region is duplicated and placed at the left hand end of the generated DNA molecule (FIG. 6). The resulting structure U3-R-U5 is called LTR (Long Terminal Repeat) and is thus identical and repeated at both ends of the DNA structure or provirus. The U3 region at the left hand end of the provirus harbours the promoter (see below). This promoter drives the synthesis of an RNA transcript initiating at the boundary between the left hand U3 and R regions and terminating at the boundary between the right hand R and U5 region (FIG. 6). This RNA is packaged into retroviral particles and transported into the target cell to be infected. In the target cell the RNA genome is again reverse transcribed as described above.

According to the procon principle a retroviral vector is constructed in which the right hand U3 region is altered (FIG. 7), but the normal left hand U3 structure is maintained (FIG. 7); the vector can be normally transcribed into RNA utilizing the normal retroviral promoter located within the left hand U3 region (FIG. 7). However, the generated RNA will only contain the altered right hand U3 structure. In the infected target cell, after reverse transcription, this altered U3 structure will be placed at both ends of the retroviral structure (FIG. 7).

If the altered region carries a polylinker (see below) instead of the U3 region then any promoter, including those directing tissue specific expression (see below) can be easily inserted. This promoter will then be utilized exclusively in the target cell for expression of linked genes carried by the retroviral vector. Alternatively or additionally DNA segments homologous to one or more cellular sequences can be inserted into the polylinker for the purposes of gene targeting.

In the packaging cell line the expression of the retroviral vector is regulated by the normal unselective retroviral promoter (FIG. 7). However, as soon as the vector enters the target cell promoter conversion occurs, and the therapeutic genes are expressed from a tissue specific promoter of choice introduced into the polylinker (FIG. 7). Not only can virtually any tissue specific promoter be included in the system, providing for the. Selective targeting of a wide variety of different cell types, but additionally, following the conversion event, the structure and properties of the retroviral vector no longer resembles that of a virus. This, of course, has extremely important consequences from a safety point of view, since ordinary or state of the art retroviral vectors readily undergo genetic recombination with the packaging vector to produce, potentially pathogenic viruses. Promoter conversion (Procon) vectors do not resemble retroviruses because they no longer carry U3 retroviral promoters after conversion thus reducing-the possibility of genetic recombination.

Objects of the Invention

It is an object of the present invention to provide novel usages for the nucleotide and amino acid sequences comprising Naf activity.

It is a further object of the present invention to provide novel usages for the nucleotide and amino acid sequences comprising Sag activity.

It is also a further object of the present invention to provide novel vectors useful for gene therapy of viral infections.

It is still a further object of the present invention to provide novel vectors useful for gene therapy of diseases associated with B cells.

SUMMARY OF THE INVENTION

According to one aspect of the present invention there is provided a novel usage of a nucleotide sequence or amino acid sequence of a derivative thereof comprising Naf activity for repressing the expression of viral promoters, e.g., for the treatment of viral infections.

In another aspect the invention provides a novel recombinant DNA vector for introducing into an eucaryotic cell DNA for repressing the expression of heterologous viral promoters, the vector comprising, in operable linkage, a) the DNA of or corresponding to at least a portion of a vector, which portion is capable of infecting and directing the expression in the target cells; and b) one or more coding sequences wherein at least one sequence encodes for a peptide (protein) with Naf activity or a derivative thereof. Optionally, the recombinant vector of the present invention can include at least one sequence encoding a therapeutic and/or non-therapeutic peptide (protein). For example, the peptide (protein) can be (β-galactosidase, neomycin, alcohol dehydrogenase, puromycin, hypoxanthine phosphoribosyl transferase (HPRT), hygromycin, secreted alkaline phosphatase, Herpes Simplex Virus thymidine kinase, cytosine deaminase, guanine phosphoribosyl transferase (gpt), cytochrome P 450, cell cycle regulatory genes which codes for proteins including P.T.O. or SDI, tumor supressor gene which codes for proteins including p53, antiproliferation genes which codes for proteins including melittin and cecropin, or genes which codes for cytokines) such as IL-2.

Said vector is selected from the group of viral and plasmid vectors. In particular said viral vector is selected from the group of RNA and DNA viruses. Said plasmid vector is preferably selected from the group of eucaryotic expression vectors and wherein said RNA virus vector is selected from retrovirus vectors. Said DNA virus is preferably selected from the group of adenoviruses, adenovirus associated viruses and herpes viruses; and wherein said retroviral vector is preferably selected from the group of procon vectors. In a preferred embodiment the retroviral genome is replication-defective.

In one embodiment the present invention uses the principle of promoter conversion typical for retroviruses.

The procon vector includes preferably, in operable linkage, a 5'LTR region; one or more of said coding sequences wherein at least one sequence encodes for a peptide with Naf activity or a derivative thereof for repressing the expression of heterologous viral promoters; and a 3'LTR region; said 5'LTR region comprising the structure U3-R-U5 and said 3'LTR region comprising a completely or partially deleted U3 region wherein said deleted U3 region is replaced by a polylinker sequence, followed by the R and U5 region to undergo promoter conversion.

In a further preferred embodiment, the retrovirus vector includes, in operable linkage, a 5'LTR region and a 3'LTR region, said 5'LTR region comprising the structure U3-R-U5 and said 3'LTR region comprising a completely or partially deleted U3 region wherein said deleted U3 region is replaced by one or more of said coding sequences wherein at least one sequence encodes for a peptide with Naf activity expressed from either the viral or a heterologous promoter for repressing the expression of heterologous viral promoters followed by the R and U5 region.

With reference to the procon vectors,.said polylinker sequence carries at least one unique restriction site and contains preferably at least one insertion of a heterologous DNA fragment. Said heterologous DNA fragment is preferably selected from regulatory elements and promoters, preferably being target cell specific in their expression.

For a complete disclosure of the procon vectors, the content of the Danish application DK1017/94, filed on Sep. 2, 1994 is completely included within the present application or incorporated herein by reference.

The recombinant DNA vectors provided by the present invention may preferably be used to treat viral infections by repressing viral promoters.

The recombinant DNA vectors provided in the present invention may be preferably used to repress heterologous viral promoters selected from HIV or MLV promoters.

In a further aspect the invention provides a novel usage of a nucleotide sequence or amino acid sequence or a derivative thereof comprising Sag activity in the gene therapy of disorders associated with B or T cells.

In a preferred embodiment, a recombinant DNA vector for introducing into a B or T cell DNA for gene therapy of disorders associated with B or T cells is provided, comprising, in operable linkage,
  a) the DNA of or corresponding to at least a portion of a vector, which portion is capable of infecting and directing the expression in the B or T cells; and
  b) one or more coding sequences wherein at least one sequence encodes for a peptide with Sag activity or a derivative thereof and at least one sequence encodes for a therapeutic peptide or protein.

Said vector is selected from the group of viral and plasmid vectors. In particular said viral vector is selected from the group of RNA and DNA viruses. Said plasmid vector is preferably selected from the group of eucaryotic expression vectors and wherein said RNA virus vector is selected from retrovirus vectors. Said DNA virus is preferably selected from the group of adenoviruses, adenovirus associated viruses and herpes viruses; and wherein said retroviral vector is preferably selected from the group of procon vectors. In a preferred embodiment the retroviral genome is replication-defective.

In a preferred embodiment said procon vector includes, in operable linkage, a 51'LTR region; one or more of said coding sequences wherein at least one sequence encodes for a peptide with Sag activity or a derivative thereof and at least one sequence encodes for a therapeutic peptide; and a 3'LTR region; said 5'LTR region comprising the structure U3-R-U5 and said 3'LTR region comprising a completely or partially deleted U3 region wherein said deleted U3 region is replaced by a polylinker sequence, followed by the R and U5 region to undergo promoter conversion.

According to a further preferred embodiment a retrovirus vector is used which includes, in operable linkage, a 5'LTR region and a 3'LTR region, said 5'LTR region comprising the structure U3-R-U5 and said 3'LTR region comprising a completely or partially deleted U3 region wherein said deleted U3 region is replaced by one or more of said coding sequences wherein at least one sequence encodes for a peptide with Sag activity or a derivative thereof and at least one sequence encodes for a therapeutic peptide (protein) expressed from either the viral or a heterologous promoter, followed by the R and U5 region.

Gene expression is regulated by promoters. In the absence of promoter function a gene will not be expressed. The normal MLV retroviral promoter is fairly unselective in that it is active in most cell types. However, a number of promoters exist that show activity only in very specific cell types. Such tissue-specific promoters will be the ideal candidates for the regulation of gene expression in retroviral vectors,.limiting expression of the therapeutic genes to specific target cells.

The target cell specific regulatory elements and promoters are preferably, but not limited, selected from one or more elements of the group consisting of HIV, Whey Acidic Protein (WAP), Mouse Mammary Tumour Virus (MMTV), β-lactoglobulin and casein specific regulatory elements and promoters, which may be used to target human mammary tumours, pancreas specific regulatory elements and promoters including carbonic anhydrase II and β-glucokinase regulatory elements and promoters, lymphocyte specific regulatory elements and promoters including immunoglobulin and MMTV lymphocytic specific regulatory elements and promoters and MMTV specific regulatory elements and promoters conferring responsiveness to glucocorticoid hormones or directing expression to the mammary gland, T-cell specific regulatory elements and promoters such as T-cell receptor gene and CD4 receptor promoter and B-cell specific regulatory elements and promoters such as immunoglobulin promoter or mb1. Said regulatory elements and promoters regulate preferably the expression of at least one of the coding sequences of said retroviral vector.

The LTR regions are preferably, but not limited, selected from at least one element of the group consisting of LTRs of Murine Leukaemia Virus (MLV), Mouse Mammary Tumour Virus (MMTV), Murine Sarcoma Virus (MSV), Simian Immunodeficiency Virus (SIV), Human Immunodeficiency Virus (HIV), Human T-cell Leukaemia Virus (HTLV), Feline Immunodeficiency Virus (FIV), Feline Leukaemia Virus (FELV) Bovine Leukaemia Virus (BLV) and Mason-Pfizer-Monkey virus (MPMV).

The Naf or Sag encoding sequences of the present invention will be placed under the transcriptional control of, for instance, the HIV promoter or a minimal promoter placed under the regulation of the HIV tat responsible element (TAR) to target HIV infected cells. Targeting will be achieved because the HIV promoter is dependent upon the presence of Tat, an HIV encoded autoregulatory protein (Haseltine, W. A., FASEB J., 5:2349–2360 (1991)).

Thus only cells infected with HIV and therefore expressing Tat will be able to produce the Naf or Sag peptide encoded by the vector. Alternatively, the Naf or Sag peptide could be expressed from T cell specific promoters such as that from the CD4 or T cell receptor gene. In order to target tumour cells, promoters from genes known to be overexpressed in these cells (for example c-myc, c-fos) may be used.

The Naf or Sag encoding sequences of the present invention may be placed also under the transcriptional control of other promoters known in the art. Examples for such promoters are of the group of SV40, cytomegalovirus, Rous sarcoma virus, β-actin, HIV-LTR, MMTV-LTR, target cell specific promoters, B or T cell specific promoters and tumour specific promoters.

In one embodiment of the invention the Naf or Sag peptide is expressed from MMTV promoters such as the $^{MMTV}$P2 promoter (Güzburg, W. H., et. al., *Nature*, 364:154–158 (1993)).

The retroviral vector is in one embodiment of the invention a BAG vector (Price, J. D., et. al., *Proc. Natl. Acad. Sci. USA*, 84:156–160 (1987)), but includes also other retroviral vectors.

According to a preferred embodiment of the invention at least one retroviral sequence encoding for a retroviral protein involved in integration of retroviruses is altered or at least partially deleted.

The vector preferably contains DNA fragments homologous to one or more cellular sequences. The regulatory-elements and promoters are preferably regulatable by trans-acting molecules.

In a further embodiment of the invention a retroviral vector system is provided comprising a retroviral vector as described above as a first component and a packaging cell line harbouring at least one retroviral or recombinant retroviral construct coding for proteins required for said retroviral vector to be packaged.

The packaging cell line harbours retroviral or recombinant retroviral constructs coding for those retroviral vector.

The packaging cell line is preferably selected from an element of the group consisting of ψ2, ψ-Crip, ψ-AM, GP+E-86, PA317 and GP+envAM-12.

After replicating the retroviral vector of the invention as described above in a retroviral vector system as described above, a retroviral provirus is provided wherein U3 or said polylinker and any sequences inserted in said polylinker in the 3'LTR become duplicated during the process of reverse transcription in the infected target cell and appear in the 5'LTR as well as in the 3'LTR of the resulting provirus, and the U5 of 5'LTR become duplicated during reverse transcription and appear at the 3'LTR as well as in the 3'LTR of the resulting provirus.

According to the invention the term "polylinker" is used for a short stretch of artificially synthesized DNA which carries a number of unique restriction sites allowing the easy insertion of any promoter or DNA segment. The term "heterologous" is used for any combination of DNA sequences that is not normally found intimately associated in nature. The retroviral vector of the invention refers to a DNA sequence retroviral vector on the DNA sequence level.

The invention includes, however, also mRNA of a retroviral provirus according to the invention and any RNA resulting from a retroviral vector according to the invention and cDNAs thereof.

A further embodiment of the invention provides non-therapeutical or therapeutical method for introducing Naf or Sag sequences into human or animal cells in vitro and in vivo comprising transfecting a packaging cell line of a retroviral vector system according to the invention with a retroviral vector according to the invention and infecting a target cell population with recombinant retroviruses produced by the packaging cell line.

The retroviral vector, the retroviral vector system and the retroviral provirus as well as RNA thereof may be used for producing a pharmaceutical composition for somatic gene therapy in mammals including humans. Furthermore, they are used for targeted integration in homologous cellular sequences.

The retroviral promoter structure is termed LTR. LTR's carry signals that allow them to jump in and out of the genome of the target cell. Such jumping transposable elements can also contribute to pathogenic changes. Retroviral vectors vectors can carry modified LTRs that no longer carry the signals required for jumping. Again this increases the potential safety of these vector systems.

Further objects, features and advantages will be apparent from the following description of preferred embodiments of the invention.

The splice donor (SD) at the 5.' end of the gag gene and a second splice donor (SD) are indicated as is the splice acceptor (SA) for ORF. PCR primers +1702 and −3228 used to demonstrate the transcript that utilized the second splice donor in the gag gene are shown as arrows below pORFexp. Also shown is part of the determined sequence (SEQ ID NO: 1) of the PCR product from the splice junction region which confirms the use of the second splice donor in the gag and the splice acceptor in the ORF.

Figure 2A:
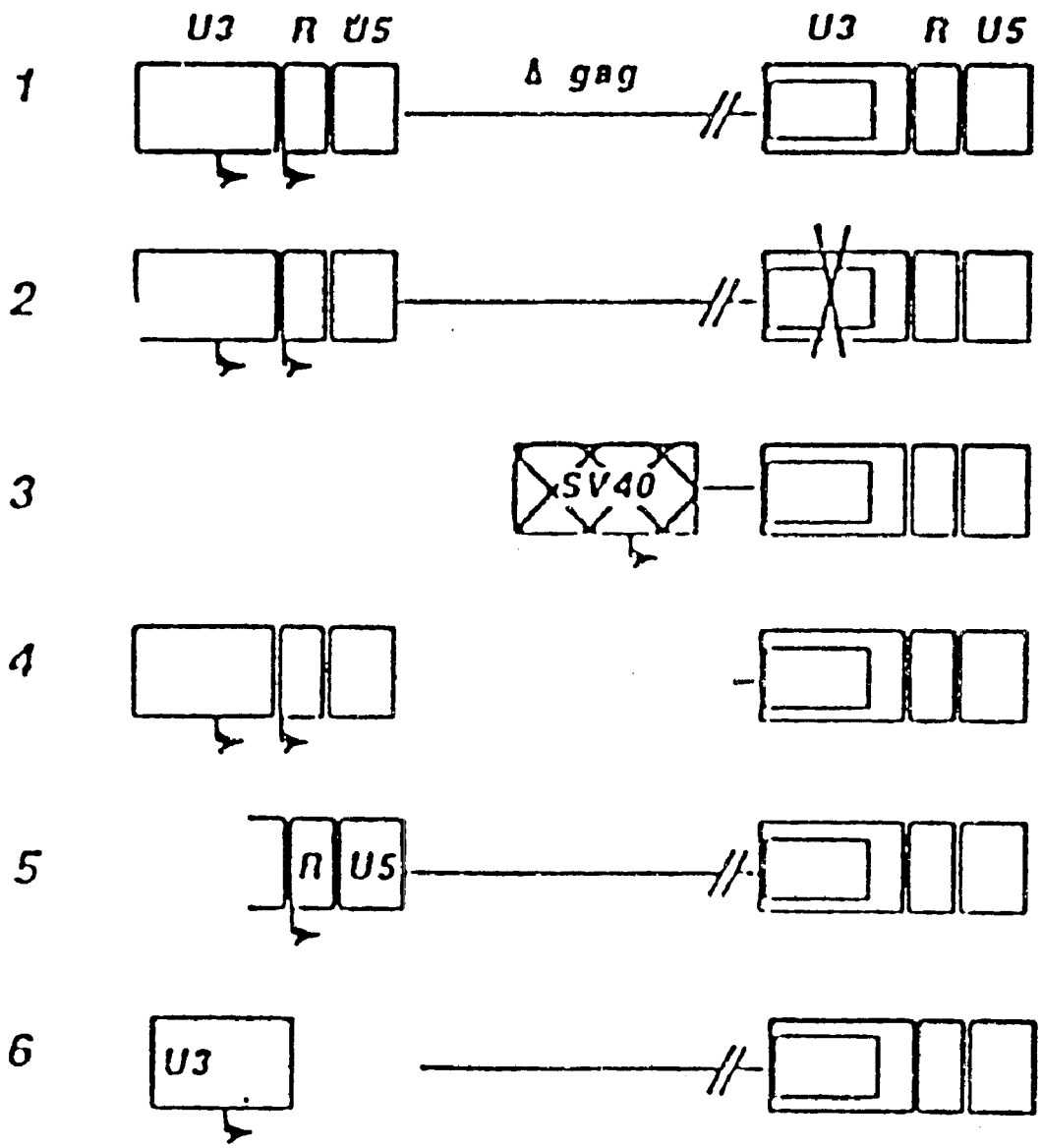

FIG. 2A is a schematic of the following expression constructs derived from pORFexp (construct 1) construct No. 2 pORFexp o/c which carries a premature termination codon within the open reading frame carried within the 3'MMTV LTR (indicated by X); construct No. 3 pSVorfexp in which ORF products are transcribed directly from a SV40 promoter; construct No. 4 pdelgag in which the gag region has been removed; construct No. 5 pdelU3 carrying only the classic MMTV promoter; and construct No. 6 pdelRU5 carrying the only novel promoter.

Figure 2B:
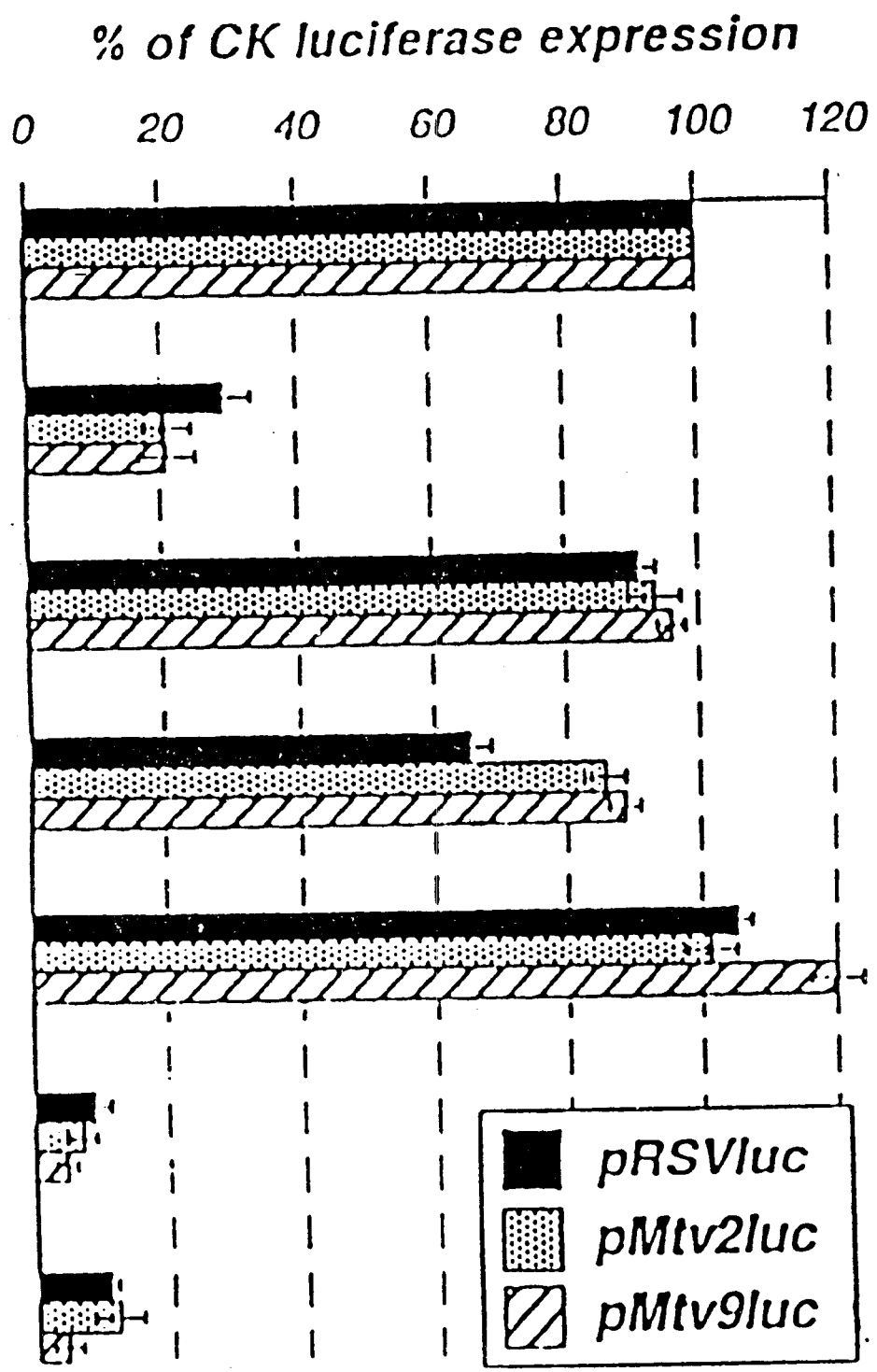

FIG. 2B is a graph showing the mean value of 3 independent experiments in which luciferase activity from the indicator constructs pRSVluc (solid bars), pMtv2luc (dotted bars) and pMtv9luc. (striped bars) was measured after transient transfection into either CK cells or cell clones that have stably acquired the indicated expression constructs. At least two individual clones carrying each construct were tested in the luciferase assay to rule out clonal variation effects.

Figure 2C:
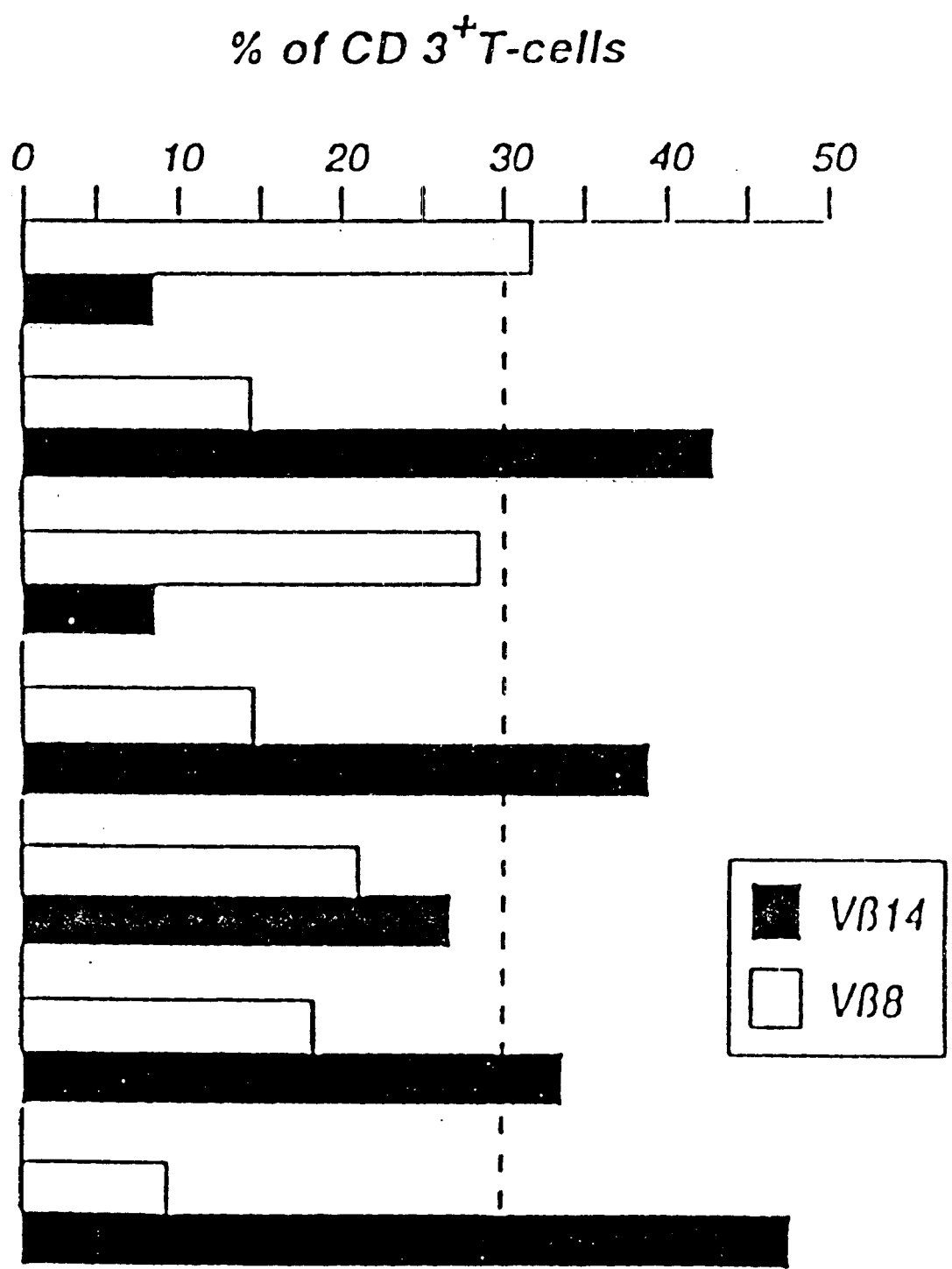

FIG. 2C is a graph showing the ability of each of the expression constructs to direct superantigen activity after electroporation into A20 cells in a mixed lymphocyte reaction. The 3'LTR of these constructs is derived from the Mtv-2 provirus, the superantigen of which stimulates specifically the growth of Vβ14 bearing T cells (Güzburg, W. H. et al., *Nature*, 364:154–158 (1993), Acha-Orbea, H., et al., *Nature*, 350:207–211 (1991) and Hornsby, P. et. al., *Bio Techniques*, 12:244–251 (1992)). The percentage of Vβ14 bearing T cells (solid bars) in the total population of T cells (CD3+cells) is shown as is the percentage of nonresponding, Vβ8 bearing, T cells (open bars). An increase in Vβ14 bearing T cells and a concomitant decrease in Vβ8 bearing T cells is indicative of Mtv-2 superantigen activity.

Figure 3:
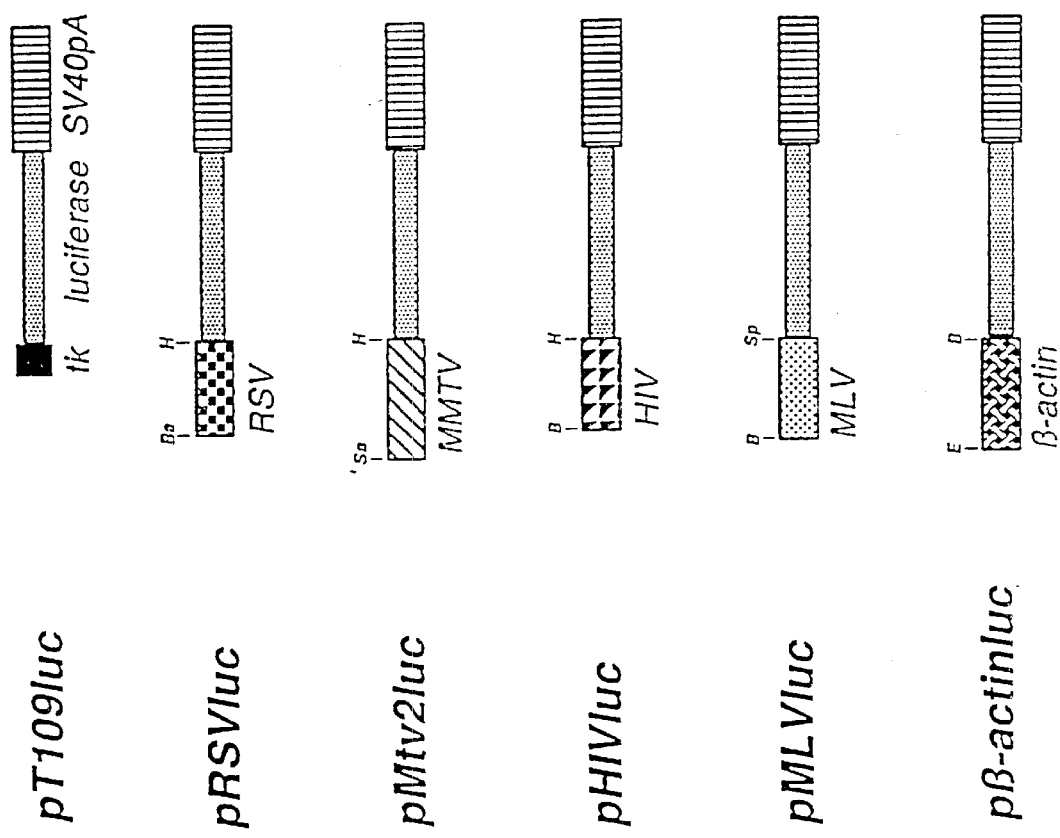

FIG. 3 is a schematic of indicator constructs used to measure Naf medicated downregulation. All of the constructs carry a promoterless luciferase gene coupled to the indicated heterologous promoters and transcription termination sequences from SV40 (SV4opA). Relevant restriction enzyme sites are indicated: BamHI(Ba), BglII (B), HindIII (H), SalI(Sa), SpeI(Sp) and EcoRI (E).

Figure 4:
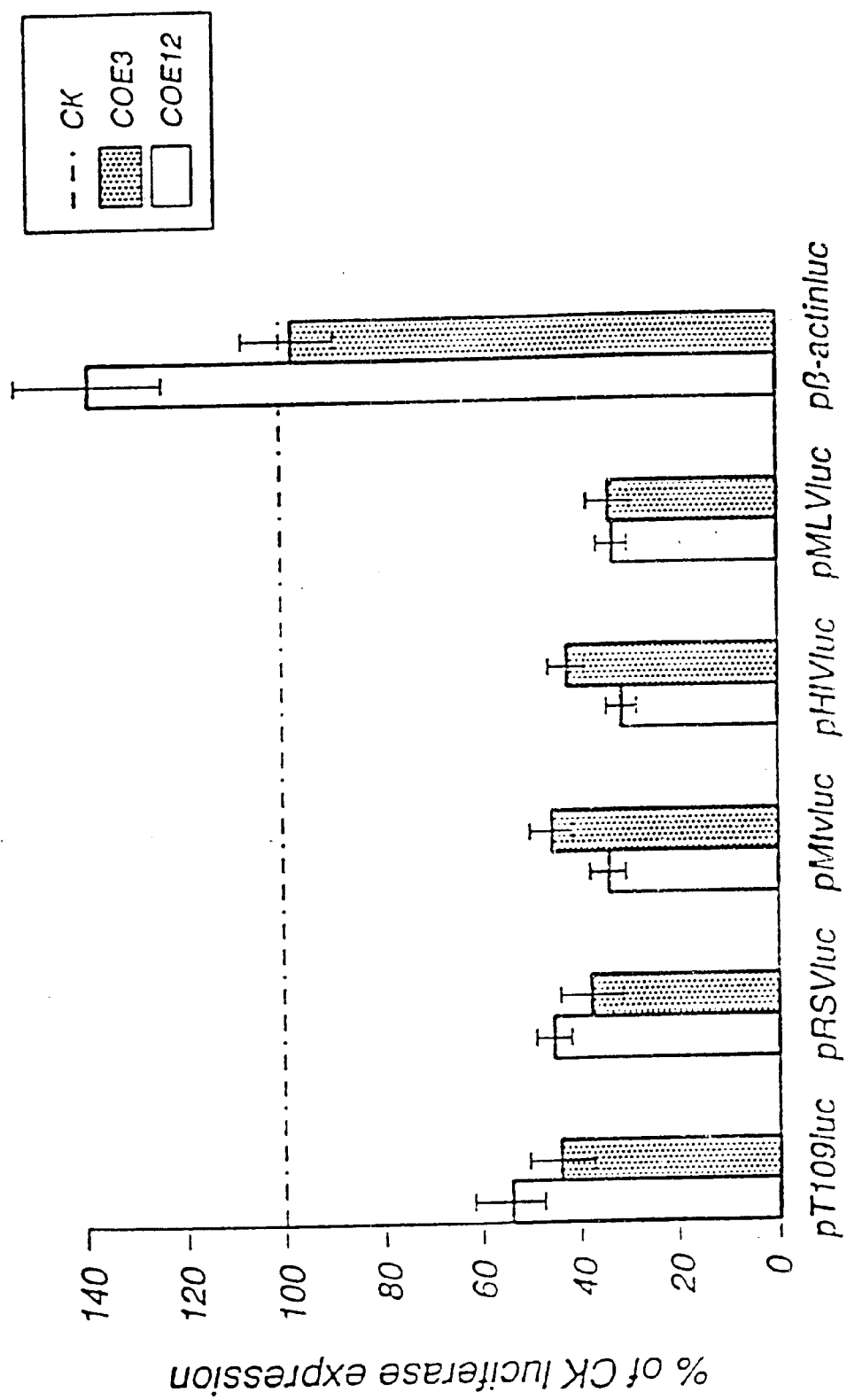

FIG. 4 is a bar graph showing down regulation of luciferase expression from the HSVtk (pT109luc), RSV (pRSVluc), MMTV (pMtvluc), HIV (pHIVluc), MLV (pMLVluc) but not the β-actin (pβ-actinluc) promoter by Naf. CK, COE3 and COE12 cells were transiently transfected with the indicated plasmids and cell extracts prepared 48 hours post transfection. Equivalent amounts of protein were used for luciferase assay as described (Hornsby, P. et. al., *Bio Techniques*, 12:244–251 (1992)). The luciferase activity of each construct in CK cells was taken as 100% (dotted line) and the mean and range of 3 independent experiments is shown for COE3 (dotted boxes) and CEO12 (open boxes).

Figure 5:
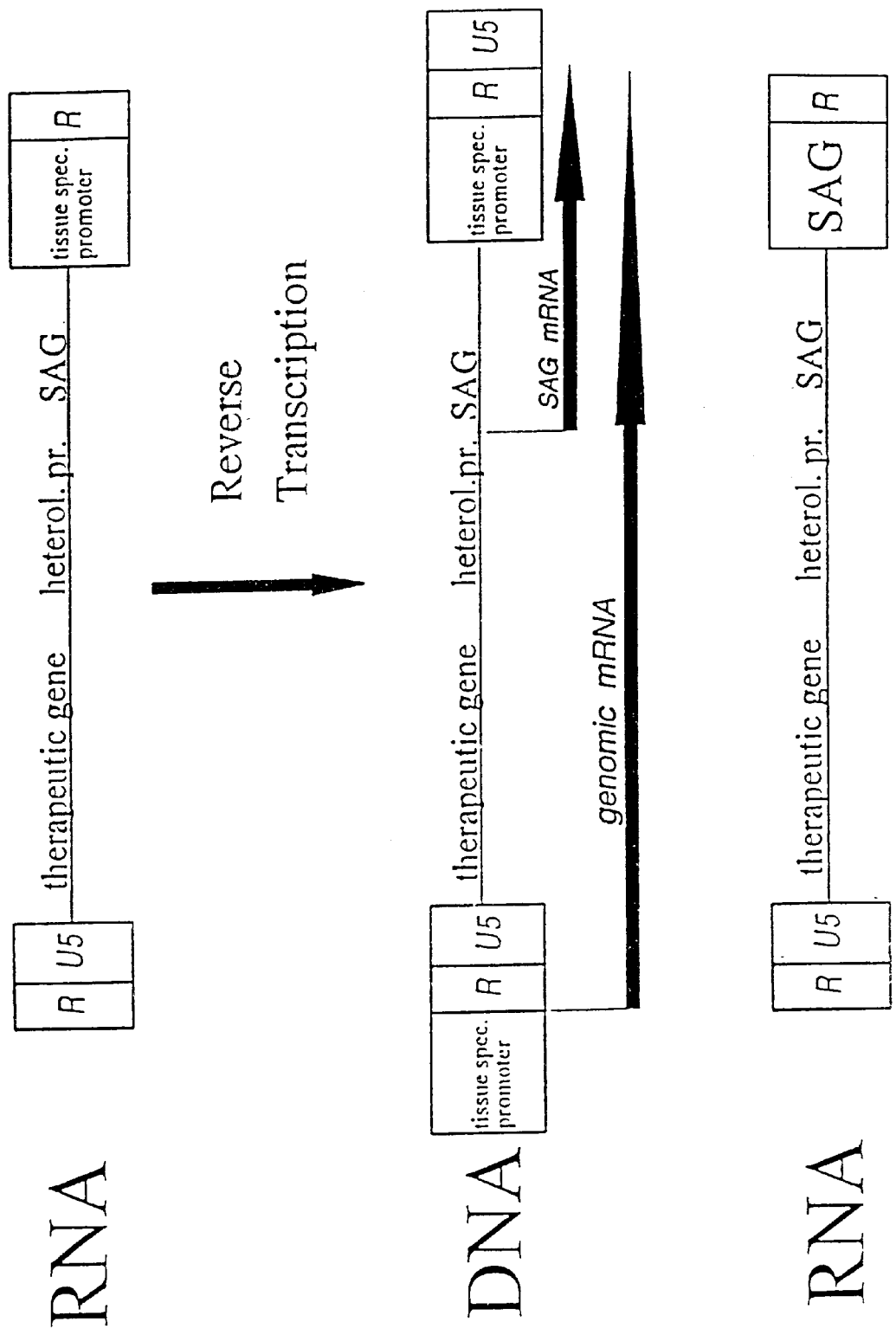

FIG. 5 is a schematic drawing showing a retroviral vector according to one embodiment of the invention wherein at least part of the U3 region is replaced by a Sag coding sequence or a derivative thereof.

Figure 6:
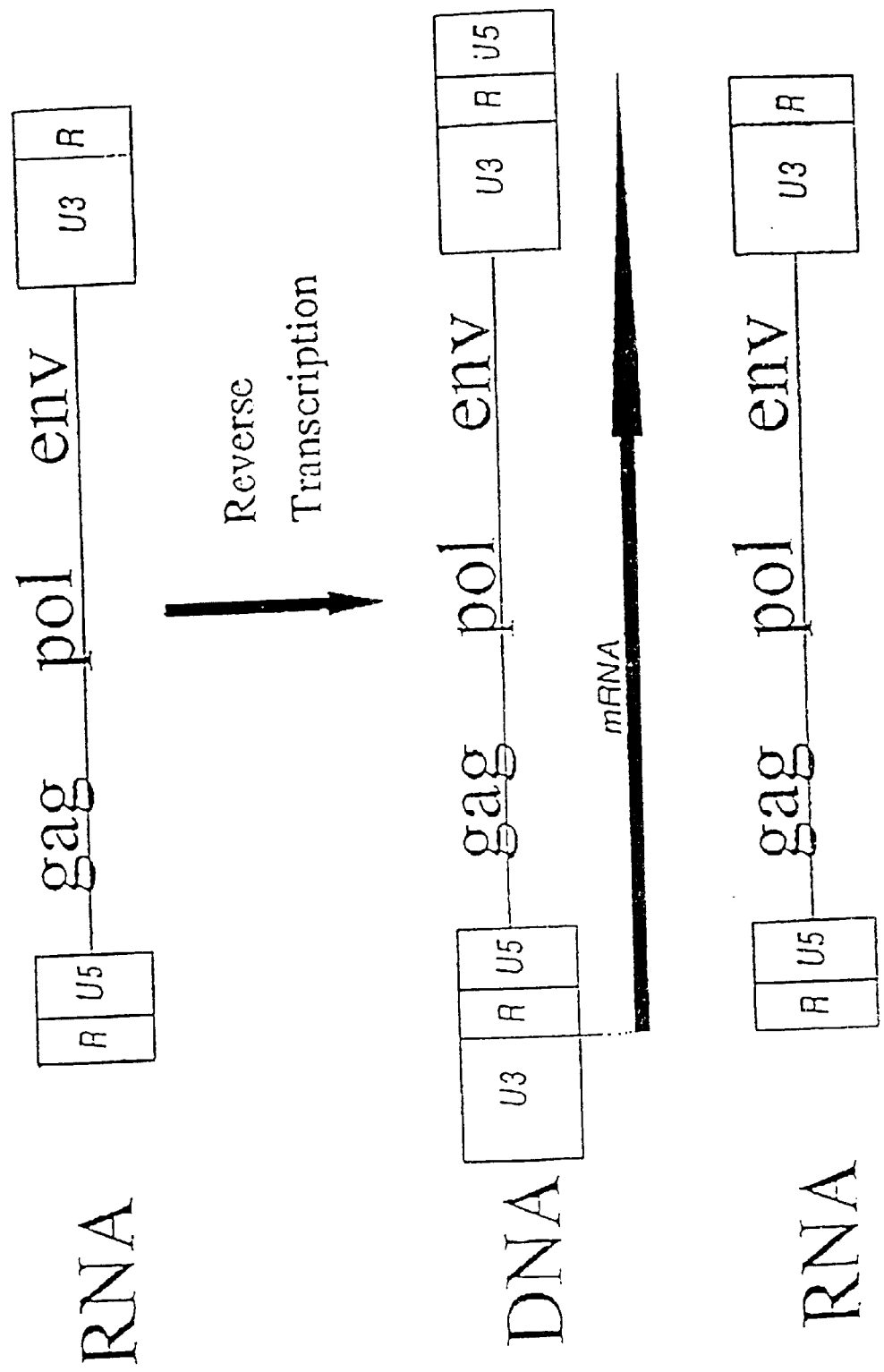

FIG. 6 is a schematic of reverse transcription of a retroviral genome.

Figure 7:
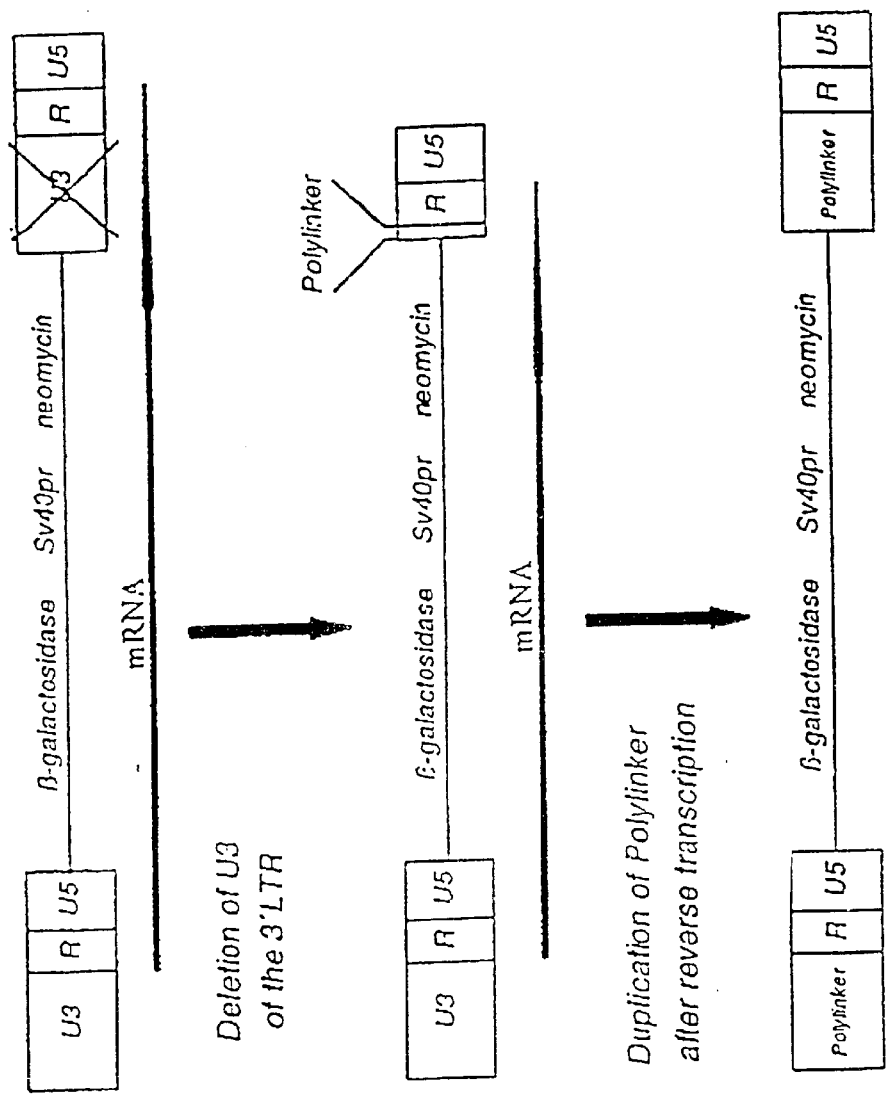

FIG. 7 is a schematic of the procon principle wherein a U3 minus BAG-vector is constructed.

DETAILED DESCRIPTION OF THE INVENTION

The invention refers to novel recombinant vectors useful for gene therapy of viral infections and of diseases associated with B and T cells. The present invention relates, furthermore, to novel usages of the two products of the open reading frame of mouse mammary tumour virus.

The superantigen activity, encoded by the MMTV ORF appears to be crucial for the transfer of MMTV from the gastric tract where the virus is delivered in the milk, to the mammary gland. One of the first cells to become infected by the ingested MMTV are B cells. These infected B cells express the virally encoded Sag, possibly from a recently described, second viral promoter (Güzburg, W. H. et al., *Nature*, 364:154–158 (1993)) on the cell surface. This presentation of Sag protein in combination with MHC class II molecules results in the stimulation of specific classes of T cells according to the V13 chain that they carry as part of the T cell receptor. Such activated T cells are stimulated to produce cytokines which then cause the local proliferation of B cells, which includes the original MMTV infected B cells (reviewed in (Acha-Orbea, H., et al., *Nature*, 350:207–211 (1991)). Thus the initial few infected B cells are amplified and form a reservoir which eventually passes the virus on to the mammary gland.

It was surprisingly shown that the expression of the MMTV encoded superantigen from a retroviral or other type of vector system carrying an additional, B or T cell specific therapeutic gene permits the expansion of B or T cells bearing the introduced genes. Thus superantigen may be used to enrich in vivo genetically modified B cells by using a naturally occurring amplification mechanism. This increases the efficiency of gene transfer to B or T cells.

As shown herein,. Naf acts in trans to downregulate expression from MMTV by reducing the rate of transcription (Salmons, B., et al., *J. Virol.*, 64:6355–6359, (1990)). Surprisingly, as also shown herein, the effects of Naf are not limited to MMTV; Naf represses also the expression of a number of retroviral promoters including those of Human Immunodeficiency virus (HIV) and Murine Leukemia Virus (MLV). This provides evidence that Naf induced down regulation is mediated by a common transcription factor (FIG. 4). The ability of Naf to negatively regulate retroviral promoters enables use of Naf in gene therapy towards the treatment of viral infections, in particular of HIV infections. One such strategy involves the delivery of a Naf expression system (for example in a retroviral or other gene transfer vector systems) specifically to HIV infected cells from AIDS patients, in order to inhibit virus expression and replication. Further, Naf may also be useful as a means for controlling the expression from MLV based retroviral vectors in other gene therapy protocols.

The following examples will illustrate the invention further. These examples are however in no way intended to limit the scope of the present invention as obvious modifications will be apparent, and still other modifications and substitutions will be apparent to anyone skilled in the art.

The recombinant DNA methods employed in practicing the present invention are standard procedures, well known to those skilled in the art, and described in detail, for example, in Molecular Cloning, Sambrook, et,. al., Cold Spring Harbor Laboratory, (1989) and B. Perbal, A Practical Guide to Molecular Cloning, John Wiley & Sons (1984).

Materials and Methods Plasmids a) Expression Constructs

Figure 1:
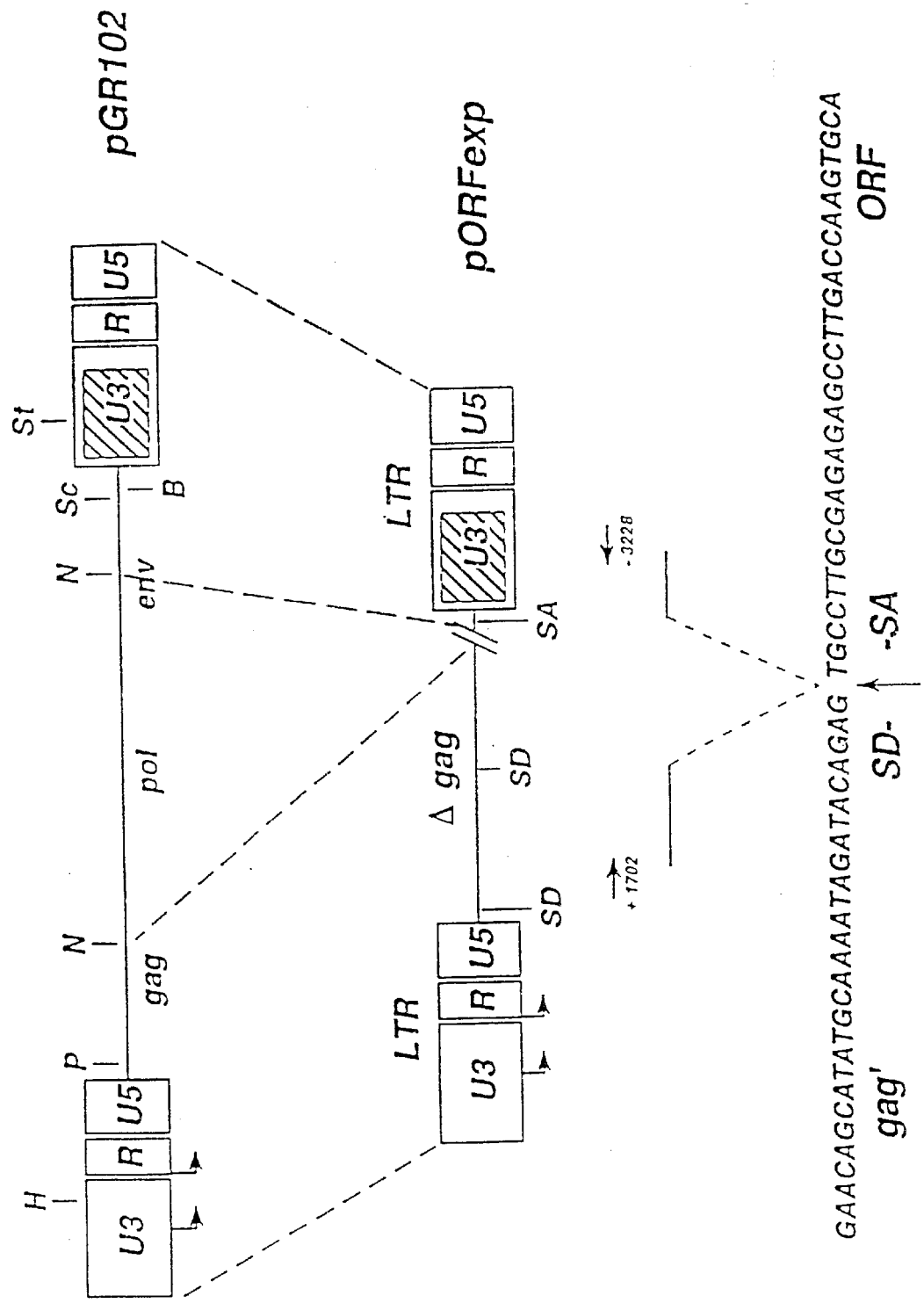
FIG. 1 is a schematic of the MMTV Naf/Sag expression plasmid pORFexp. The pORFexp plasmid was derived from pGR102 (upper construct), which contains a complete biologically active MMTV provirus (Salmons, B. et. al., *virology*, 144:101–114 (1985)), by digestion with NcoI(N) to remove the part of the gag as well as the pol and env regions followed by religation. Indicated are the U3, R and U5 regions of the LTR as well as the gag, pol and env genes and the two transcriptional starts (arrowed) within the 5'LTR. The open reading frame is indicated by the shaded box in the U3 region. Restriction enzyme cleavage sites for HpaI(H), PvuII(P), ScaI(Sc), BglII(B) and StuI(St) used in the construction of the pORFexp derived plasmids pORFexp o/c (No. 2 in FIG. 2A), pdelU3 (No. 5 in FIG. 2A), pdelRU5 (No. 6 in FIG. 2A), pdelgag (No. 4 in FIG. 2A) and pSVorfexp (No. 3 in FIG. 2A);, (FIG. 3) are also indicated.

The pORFexp expression plasmid was constructed by digesting pGR102 (Salmons, B. et. al., Virology, 144:101–114 (1985)) with NcoI to remove part of the gag, pol and env sequences followed by religation (FIG. 2A). A series of plasmids were derived from pORFexp (FIG. 1); pORFexp o/c (construct 2; FIG. 2A) carries a ClaI linker at the StuI site in the 3'LTR (FIG. 1) creating a premature stop codon leading to a truncation of the predicted ORF product (Salmons., B., et al., J. Virol., 64:6355–6359, (1990)); pdelgag (construct, 4; FIG. 2A) by digestion of pORFexp with PvuII and ScaI (FIG. 1) followed by religation; pdelU3 (construct 5; FIG. 2A) by digestion of pORFexp with EcoRV (in the 5'vector sequences) and HpaI (FIG. 1) to remove most of the U3 region including the novel upstream promoter in the 5'LTR, followed by religation; pdelRU5 (construct 6; FIG. 2A) by the removal of a HpaI/PvuII fragment from pORFexp (FIG. 1), which deletes a small part of the U3, the R and U5 regions of the 5'LTR thereby removing the classic promoter but leaving the novel promoter intact; pSVorfexp (construct 3; FIG. 2A) by ligation of the BglII/XmnI SV40 promoter containing fragment of pSV2neo (Southern, P. J. and Berg, P., J. Mol. App. Gen., 1:327–341:(1982)) to a BglII/XmnI 3'LTR containing fragment of pORFexp (FIG. 1).

b) Indicator Constructs

Expression plasmids carrying the luciferase gene under the transcriptional control of a number of heterologous promoters (FIG. 3) were used to determine whether these promoters are Naf responsive: pT109luc (Nordeen, S. K., Biotechniques, 6:454–458 (1988)) carries a 132 bp BamHI-BglII fragment of the herpes simplex virus thymidine kinase promoter; pRSVluc carries a 550 bp BamHI-HindIII fragment comprising the promoter of Rous Sarcoma Virus (RSV) contained in the LTR; pMtv2luc was constructed in the following way. The HpaII site of a BglII-HpaII DNA fragment containing the complete MMTV LTR from an exogenous milk borne virus was converted into a BamHI site and the resultant fragment cloned into the BamHI site of pUC18. A SalI-HindIII fragment of the resulting plasmid was then cloned into the plasmid pLUC1, which carries a promoterless luciferase gene (Günzburg, W. H. et al., Nature, 364:154–158 (1993)). pMtv9luc carries a 1200 bp PstI-EcoRi DNA fragment containing the entire LTR of the endogenous Mtv-9 provirus linked to the luciferase gene (Lund, F. E. and Corley, R. B., J. Exp. Med., 174:1439–1450 (1991)); pHIVluc was constructed by cloning a. 560 bp BglII-HindIII DNA fragment of the human immunodeficiency virus (HIV-1) LTR lacking the NRE into the same sites of pLUC1; pMLVluc carries the complete murine leukemia virus (MLV) LTR within a 704 bp BglII-SpeI DNA fragment from a recombinant polymerase chain reaction (PCR) (using the primers 5' CGCAGATCTTAGCTTAAG-TAACGCCATT3' (SEQ ID NO: 2) and 5' CGCACTAGT-TCCGCCAGATACAGAG3' (SEQ ID NO: 3)) ligated into the same sites in pLUC1; p13-actinluc (Langer, S. J. and Ostrowski, M. C., Mol. Cell. Biol., 8:3872–3881 (1988)) carries a EcoRI-BamHI 13-actin promoter containing DNA fragment from the plasmid pHβAPr-1-neo coupled to the luciferase gene.

RT-PCR Analysis

RNA was isolated from transfected cells, reverse transcribed into DNA and used in PCR reactions as previously described (Güzburg, W. H. et. al., Nature, 364:154–158 (1993). The primers +1702 (5'GAGGTACGCAGC GGAACA3') (SEQ ID NO: 4) and −3228 (5'TGATGGGCTCATCCGTTT3') (SEQ ID NO: 5), specific for the gag and ORF region (FIG. 1) were used for PCR reactions and resultant products were sequenced using the same primers on an ABI-373A automated DNA sequence (Applied Biosystems).

Cell Culture

A20 cells, derived from a B-cell lymphoma of a Balb/c mouse (2G), were cultured in RPMI medium containing 5% fetal bovine serum, L-glutamine and mercaptoethanol. CK cells, derived from the feline kidney cell line CFRK (Crandell, R. A. et. al., In vitro 9, 1:76–185 (1973), and GR mouse mammary carcinoma cells, productively infected with MMTV (Salmons, B. et. al., Virology, 144:101–114 (1985)) were maintained in Dulbecco's MEM containing 10% fetal bovine serum.

Transfection

CK cells, seeded at a density of $5\times10^5$ cells per 10 cm dish, were co-transfected with 5 μg of pORFexp and 0.5 μg pRSVneo using the Cellphect kit (Pharmacia) according to the manufacturers instructions. Stably transfected G418 resistant (400 μg/ml) cell clones were isolated two weeks post transfection. Two of these clones, COE3 and COE12, were shown to carry and express the pORFexp construct. Each of the various pORFexp derived expression constructs were also co-transfected into CK cells at a 20:1 ratio with pX343, a plasmid conferring hygromycin resistance. Stably transfected hygromycin resistant cell clones or populations were isolated 15–17 days after transfection and selection in 100 μg/ml hygromycin. Transfected clones were used for supertransfection with 5 μg of the luciferase carrying constructs.

Luciferase Assay

Cell extracts were prepared for luciferase assays 48 hours post transfection as described previously (Hornsby, P. et. al., Bio Techniques, 12:244–251 (1992)). The protein concentration of the samples was determined by the Bradford assay technique (Bio-Rad, Protein Assay) and 100 ng of protein used for the luciferase assay as described previously (Hornsby, P. et. al., Bio Techniques, 12:244–251 (1992)) using a Berthold AutoLumat LB953.

Superantigen Assay $1\times10^7$ A20 cells were resuspended in RPMI containing 20 μg of plasmid in a 0.4 cm cuvette and pulsed with 300V 960 μF (Bio-Rad Gene Pulser) as described previously (Wintersperger, S. et. al., BioTechniques, 16:882–886 (1994)). Twenty hours later, the cells were irradiated (3000 rad) to inhibit growth and $1\times10^7$ Cocultured with $2\times10^6$ primary T cells freshly isolated from popliteal lymph nodes of Balbic mice. Four days later, T cells were stained with R-phycoerythrin labelled anti-CD3mAb and either FITC conjugated antiV8 or antiVβ14 mAb and analyzed by FACS (Elite, Coulter Inc.) to determine the percentage of V8 and Vβ14 bearing T cells.

S1 Analysis

Total RNA (40 μg) isolated from CK cells, CK cells transfected with pdelgag, pORFexp o/c or pORFexp or GR cells was hybridized to a BstEII probe as previously described (Güzburg, W. H. et al., Nature, 364:154–158 (1993)). Transcripts initiating at the MMTV promoter protect a fragment of 110 nt. The protected fragments were densitometrically evaluated using a Fuji Phosphoimager and the intensity of the 110 nt fragment was corrected using the loading control to ensure equal amounts of counts were applied to each lane.

Establishment of Naf Expressing Clones

Previous studies implicated both gag and ORF sequences -as encoding Naf (Salmons, B., et al., *J. Virol.,* 64:6355–6359, (1990)). To verify this data, a plasmid, pORFexp, was constructed which carries putative Naf encoding sequences (FIG. 1). Naf mediated transcriptional downregulation was observed upon transfection of pORFexp into RMC2h assay cells (Salmons, B., et al., *J. Virol.,* 64:6355–6359, (1990)). In order to facilitate the detection of potential Naf specific transcripts as well as to further characterize Naf activity, the pORFexp construct was transfected into CK cells, one of the few cultured cell lines that are permissive for MMTV (Salmons, B. et. al., *Virology,* 144:101–114 (1985); Crandell, R. A. et. al., *In vitro* 9, 1:76–185 (1973)). A number of resultant cell clones, including COE3 and COE12 (see below), were shown to carry the pORFexp construct in a contiguous form. Transcripts expressed in the pORFexp clones were examined by Northern blot as well as by RT-PCR (FIG. 1). In addition to the previously described MMTV splice donor at the 5' end of the gag gene (FIG. 1), a novel splice donor within the gag gene was identified. Transcripts using this splice donor also use the previously described splice acceptor for ORF (FIG. 1). A second promoter has recently been described within the U3 region of the MMTV LTR (Güzburg, W. H. et al., *Nature,* 364:154–158 (1993)). Transcripts initiating at this promoter and utilizing the novel splice donor within the gag gene generate mRNAs of 2.5 kb. ORF specific transcripts of a similar size have been previously reported (Lund, F. E. and Corley, R. B., *J. Exp. Med.,* 174:1439–1450 (1991); Held, W. et. al., *J. Exp. Med.,* 177:359–366 (1993); Lund, F. E. et. al., *J. Immunol.,* 150:78–86 (1993)). The two pORFexp transfected cell clones COE3 and COE12 were further analyzed for functional Naf activity.

Naf Down Regulates Heterologous Viral Promoters

Naf was originally demonstrated to downregulate expression from an MMTV provirus in which the 5'LTR had been replaced by that of Rous sarcoma virus (RSV) (Salmons, B. et. al., *J. Virology,* 64:6355–6359 (1990)). Thus it was not known whether Naf induced downregulation was mediated by sequences in the RSV promoter or in the linked MMTV provirus. To resolve this issue two constructs in which either the MMTV or RSV LTR is linked to a promoterless luciferase gene (FIG. 3) were transfected into both COE clones as well as into CK cells. The luciferase activity from each construct (pRSVluc and Mtvluc) in two COE clones was around 40% of that observed in CK cells (FIG. 4), whereas luciferase activity from a control β-actin promoter was not reduced.

Surprisingly, it could be demonstrated that both COE clones express functional Naf and that both retroviral promoters are Naf responsive and that Naf downregulates expression from other heterologous retroviral promoters. This could be verified for the promoters carried within the HIV and MLV LTRs (FIG. 4). Surprisingly, the HSVtk promoter was also Naf responsive. Clearly, the downregulatory effects are not due to clonal variation since the extent of luciferase downregulation from each construct was similar in both COE clones. Further, the finding that the β-actin-luciferase construct was not downregulated-strongly demonstrates that this is not a nonspecific property of the COE clones. The observation that Naf represses transcription from heterologous promoters as well as from the MMTV LTR provides evidence that Naf acts indirectly via an as yet unidentified common transcription factor.

Example for the Construction of a Sag Carrying Therapeutic RNA Virus Vector

The superantigen encoding sequences are inserted into the retroviral vector either under the transcriptional control of the retroviral promoter or a heterologous promoter. The Sag can be inserted in place of the retroviral structural genes as shown in the accompanying FIG. 5 or in the U3 region of the left hand long terminal repeat (LTR). A procon vector carrying Sag is introduced into a packaging cell line, recombinant virus is produced and used to infect the target cells. Upon infection, the viral genomic RNA is reverse transcribed into a double stranded DNA form, which results is the placement of the Sag sequences in both LTRs, and the DNA is then integrated in the host cell genome where it is expressed like any other cellular gene. A therapeutic gene may in addition to the Sag also be carried by the retroviral vector.

T Cell Amplification

It is thought that in addition to B cells, other cell types are able to present superantigens, including T cells (Janeway, *Current Biology,* 1, (1991); Goodglick and Braun, (1994)). It is also known that T cells may present superantigens to other T cells thereby causing the stimulation of the presenting T cells. According to one embodiment of the invention retroviral vectors carrying Sag may also be used to amplify T cells carrying T cells relevant therapeutic genes, in an analogous fashion to that described for B cells.

The present invention provides novel recombinant DNA vectors for gene therapy including a transcriptional unit for the negative acting factor of MMTV to downregulate the expression of heterologous promoters, in particular HIV and MLV promoters.

In a further embodiment the invention provides novel recombinant DNA vectors for gene therapy including both a transcriptional unit for the superantigen activity of MMTV and a B or T cell specific therapeutic peptide or regulatory sequence for the treatment of diseases associated with B or T cells.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed:

1. A recombinant vector comprising, mouse mammary tumor virus sequences which consist of a mouse mammary tumor virus long terminal repeat open reading frame and a naf activity sequence, wherein said naf activity sequence is between an R region of a 5' long terminal repeat and a 3' end of a gag gene of the mouse mammary tumor virus thereby including a splice donor site which is in addition to the splice donor site at the 5' end of the gag gene, and wherein the remainder of the vector is derived from a vector other than a mouse mammary tumor virus.

2. An isolated RNA of the vector according to claim 1.

3. An isolated host cell comprising the vector according to claim 1.

4. A method of producing a host cell having an MMTV-LTR ORF and a sequence of an MMTV gag gene with naf activity comprising transfecting the host cell with the vector of claim 1.

5. A host cell produced by the method of claim 4.

6. A method for repressing the activity of a viral promoter other than a mouse mammary tumor viral promoter, comprising transducing a target cell comprising said promoter with the vector according to claim 1, wherein the viral promoter is repressed.

7. The recombinant vector according to claim 1, wherein said vector is a vector selected from the group consisting of: RNA virus vectors, DNA virus vectors and eucaryotic expression vectors.

8. A recombinant vector according to claim 7, wherein said vector is selected from the group consisting of: adenovirus vectors, adenovirus associated virus a vectors, herpes virus vectors and retrovirus vectors.

9. A recombinant retroviral vector system which is capable of producing a retroviral particle, comprising a retroviral vector according to claim 8 wherein the retroviral vector is replication defective and a packaging cell line comprising a retroviral or recombinant retroviral construct coding for proteins required for packaging a product transcribed from said retroviral vector.

10. An isolated retroviral particle produced by the retroviral vector system of claim 9.

11. A recombinant retroviral provirus produced by infecting a target cell with the retroviral particle of claim 10.

12. An isolated mRNA transcribed from a retroviral provirus according to claim 11.

13. A method of producing a host cell having an MMTV-LTR ORF and a sequence of an MMTV gag gene with naf activity comprising infecting the host cell with the retroviral particle of claim 10.

14. A host cell produced by the method of claim 13.

15. A method for repressing the activity of a viral promoter comprising other than a mouse mammary tumor viral promoter, infecting a target cell comprising said promoter with the retroviral particle of claim 10, wherein the viral promoter is repressed.

16. A method for introducing nucleotide sequences which encode Naf into a cell comprising infecting said cell with the retroviral particle of claim 10 and culturing the cell under conditions in which naf is expressed in said cell, thereby introducing nucleotide sequences which encode Naf into a cell.

17. The method of claim 16 wherein the cell is selected from the group consisting of: an animal cell and a human cell.

18. A recombinant retroviral vector which is capable of undergoing promoter conversion and is replication-defective comprising, in operable linkage,
  a) a 5' long terminal repeat region comprising the structure U3-R-U5 site, derived from a vector other than a mouse mammary tumor virus;
  b) mouse mammary tumor virus sequences consisting of an open reading frame having naf activity derived from a mouse mammary tumor virus long terminal repeat and a naf activity sequence, wherein said naf activity sequence is between an R region of a 5' long terminal repeat and a 3' end of a gag gene of the mouse mammary tumor virus thereby including a splice donor site which is in addition to the splice donor site at the 5' end of the gag gene;
  c) optionally, at least one sequence encoding a peptide selected from the group consisting of: β-galactosidase, neomycin, alcohol dehydrogenase, puromycin, hypoxanthine phosphoribosyl transferase (HPRT), hygromycin, secreted alkaline phosphatase, Herpes Simplex Virus thymidine kinase, cytosine deaminase, guanine phosphoribosyl transferase (gpt), cytochrome P 450, cell cycle regulatory proteins, tumor suppressor proteins, antiproliferation proteins, and cytokines; and
  d) a 3' long terminal repeat region derived from a vector other than a mouse mammary tumor virus comprising a completely or partially deleted U3 region wherein said deleted U3 region is replaced by a polylinker sequence carrying at least one unique restriction site.

19. The recombinant vector of claim 18 wherein one or more heterologous DNA fragments are inserted into said polylinker sequence, followed by the R and U5 region.

20. The recombinant vector according to claim 19 wherein said heterologous DNA fragment comprises at least one non-coding sequence selected from regulatory elements or promoters which regulate the expression of at least one of the coding sequences of said recombinant vector.

21. A mouse mammary tumor virus vector comprising a mouse mammary tumor virus long terminal repeat open reading frame, a naf activity sequence, wherein said naf activity sequence consists of a sequence of the mouse tumor virus which is between an R region of a 5' long terminal repeat and a 3' end of a gag gene of the mouse mammary tumor virus thereby including a splice donor site which is in addition to the splice donor site at the 5' end of the gag gene and non-functional mouse mammary tumor virus pol and env genes.

22. The vector according to claim 21, wherein the pol and env genes are mutated or wholly or partially deleted so that the pol and env genes are nonfunctional.

23. An isolated RNA of the vector according to claim 21.

24. An isolated host cell comprising the vector according to claim 21.

25. A method of producing a host cell having an MMTV-LTR ORF, a sequence of an MMTV gag gene with naf activity, and non-functional MMTV pol and env genes comprising transfecting the host cell with the vector of claim 21.

26. A host cell produced by the method of claim 25.

27. A method for repressing the activity of a viral promoter other than a mouse mammary tumor viral promoter comprising transducing a target cell comprising said promoter with the vector according to claim 21, wherein the viral promoter is repressed.

28. A recombinant retroviral vector system which is capable of producing a retroviral particle, comprising a retroviral vector according to claim 21 wherein the retroviral vector is replication deficient and a packaging cell line including a retroviral or recombinant retroviral construct coding for proteins required for packaging of a product transcribed from said retroviral vector.

29. An isolated retroviral particle produced by the retroviral vector system of claim 28.

30. A recombinant retroviral provirus produced by infecting a target cell with the retroviral particle of claim 29.

31. An isolated mRNA transcribed from a retroviral provirus according to claim 30.

32. A method of producing a host cell having an MMTV-LTR ORF, a sequence of an MMTV gag gene with naf activity, and non-functional MMTV pol and env genes comprising infecting the host cell with the retroviral particle of claim 29.

33. A host cell produced by the method of claim 32.

34. A method for repressing the activity of a viral promoter other than a mouse mammary tumor viral promoter comprising infecting a target cell comprising said promoter with the retroviral particle of claim 29, wherein the viral promoter is repressed.

35. A method for introducing nucleotide sequences which encode Naf into a cell comprising infecting said cell with the retroviral particle of claim 29 and culturing the cells under conditions in which naf is expressed in said cell, thereby introducing nucleotide sequences which encode Naf activity into a cell.

36. A mouse mammary tumor virus recombinant retroviral vector which is capable of undergoing promoter conversion and is replication-defective comprising, in operable linkage, a) a 5' long terminal repeat region comprising the structure U3-R-U5, derived from a vector other than a mouse mammary tumor virus;

b) mouse mammary tumor virus sequences consisting of an open reading frame having naf activity derived from a mouse mammary tumor virus long terminal repeat, a naf activity sequence wherein said naf activity sequence is between an R region of a 5' long terminal repeat and a 3' end of the gag gene of the mouse mammary tumor virus thereby including a splice donor site which is in addition to the splice donor site at the 5' end of the gag gene, and non-functional mouse mammary tumor virus pol and env genes;

c) optionally, at least one sequence encoding a peptide selected from the group consisting of: β-galactosidase, neomycin, alcohol dehydrogenase, puromycin, hypoxanthine phosphoribosyl transferase (HPRT), hygromycin, secreted alkaline phosphatase, Herpes Simplex Virus thymidine kinase, cytosine deaminase, guanine phosphoribosyl transferase (gpt), cytochrome P 450, cell cycle regulatory proteins, tumor suppressor proteins, antiproliferation proteins, and cytokines; and d) a 3' long terminal repeat region derived from a vector other than a mouse mammary tumor virus comprising a completely or partially deleted U3 region wherein said deleted U3 region is replaced by a polylinker sequence carrying at least one unique restriction site.

37. The recombinant vector of claim 36 wherein one or more heterologous DNA fragments are inserted into said polylinker sequence, followed by the R and U5 region.

38. The recombinant vector according to claim 37 wherein said heterologous DNA fragment comprises at least one non-coding sequence selected from regulatory elements or promoters which regulate the expression of at least one of the coding sequences of said recombinant vector.

39. An isolated host cell comprising an MMTV-LTR ORF and a sequence of an MMTV gag gene with naf activity, said sequences being introduced by a non-MMTV construct into said host cell, wherein the non-MMTV construct comprises MMTV sequences which consist of the MMTV-LTR ORF and a naf activity sequence, wherein said naf activity sequence is between an R region of a 5' long terminal repeat and a 3' end of a gag gene of the mouse mammary tumor virus thereby including a splice donor site which is in addition to the splice donor site at the 5' end of the gag gene.

40. An isolated host cell comprising an MMTV-LTR ORF, a sequence of an MMTV gag gene with naf activity, and non-functional MMTV pol and env genes.

41. A method for repressing activity of a viral promoter other than a MMTV promoter in cells in which said viral promoter is present, comprising a). introducing a MMTV naf activity sequence into the cells wherein the naf activity sequence consists of a mouse mammary tumor virus long terminal repeat open reading frame and a gag gene of a mouse mammary tumor virus, and said gag sequence is between an R region of a 5' long terminal repeat and a 3' end of the gag gene of the mouse mammary tumor virus; and b). maintaining the cells under conditions in which the naf sequence is expressed, thereby repressing activity of the viral promoter, wherein the viral promoter is repressed by a naf activity sequence,.

42. The method according to claim 41, wherein the naf sequence is introduced via a vector, said vector is a vector selected from the group consisting of: RNA virus vectors, DNA virus vectors and eucaryotic expression vectors.

43. The method according to claim 42, wherein said vector is selected from the group consisting of: adenovirus vectors, adenovirus associated virus vectors, herpes virus vectors and retrovirus vectors.

44. The method of claim 41 wherein the viral promoter is selected from the group consisting of: an HIV promoter, a MLV promoter and a HSVtk promoter.

* * * * *